US010717688B2

(12) United States Patent
Stevenson et al.

(10) Patent No.: US 10,717,688 B2
(45) Date of Patent: Jul. 21, 2020

(54) PROCESS FOR PRODUCING PURIFIED AROMATIC HYDROCARBONS FROM A MIXED HYDROCARBON FEEDSTREAM

(71) Applicant: SABIC GLOBAL TECHNOLOGIES B.V., Bergen op Zoom (NL)

(72) Inventors: Scott Stevenson, Houston, TX (US); Dimitri Daniëls, Geleen (NL)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 15/321,501

(22) PCT Filed: Jun. 25, 2015

(86) PCT No.: PCT/EP2015/064314
§ 371 (c)(1),
(2) Date: Dec. 22, 2016

(87) PCT Pub. No.: WO2015/197732
PCT Pub. Date: Dec. 30, 2015

(65) Prior Publication Data
US 2017/0144948 A1 May 25, 2017

(30) Foreign Application Priority Data
Jun. 26, 2014 (EP) .................... 14174373

(51) Int. Cl.
| C07C 5/41 | (2006.01) |
| C10G 45/68 | (2006.01) |
| C10G 45/58 | (2006.01) |
| C07C 2/66 | (2006.01) |
| C10G 65/04 | (2006.01) |
| C10G 69/12 | (2006.01) |
| C10G 35/04 | (2006.01) |
| C10G 47/00 | (2006.01) |

(52) U.S. Cl.
CPC ................ *C07C 5/417* (2013.01); *C07C 2/66* (2013.01); *C10G 35/04* (2013.01); *C10G 45/58* (2013.01); *C10G 45/68* (2013.01); *C10G 47/00* (2013.01); *C10G 65/046* (2013.01); *C10G 69/123* (2013.01); *C07C 2529/44* (2013.01); *C07C 2529/70* (2013.01); *C10G 2400/30* (2013.01)

(58) Field of Classification Search
CPC .............................. C07C 5/387–417
See application file for complete search history.

(56) References Cited

U.S. PATENT DOCUMENTS

| 2,898,387 A | * | 8/1959 | Teter ........................ B01J 23/40 |
| | | | 585/256 |
| 3,027,413 A | | 3/1962 | Moy et al. |
| 3,639,495 A | * | 2/1972 | Brewer ................... B01J 23/883 |
| | | | 585/241 |
| 3,770,614 A | * | 11/1973 | Graven ..................... B01J 29/40 |
| | | | 208/62 |
| 4,056,575 A | | 11/1977 | Gregory et al. |
| 4,157,356 A | | 6/1979 | Bulford et al. |
| 4,180,689 A | | 12/1979 | Davies et al. |
| 4,190,519 A | * | 2/1980 | Miller ...................... B01J 29/44 |
| | | | 208/102 |
| 4,235,701 A | * | 11/1980 | Kopf ....................... C07C 5/417 |
| | | | 208/144 |
| 4,358,364 A | | 11/1982 | Klosek et al. |
| 4,456,527 A | | 6/1984 | Buss et al. |
| 4,503,023 A | * | 3/1985 | Breck ...................... B01J 29/06 |
| | | | 423/715 |
| 4,594,145 A | * | 6/1986 | Roarty ................... C10G 59/06 |
| | | | 208/133 |
| 4,827,072 A | | 5/1989 | Imai et al. |
| 4,926,005 A | | 5/1990 | Olbrich et al. |
| 5,189,234 A | | 2/1993 | Amelse |
| 5,401,386 A | * | 3/1995 | Morrison ............... C10G 61/04 |
| | | | 208/138 |
| 6,177,600 B1 | | 1/2001 | Netzer |
| 7,259,282 B2 | | 8/2007 | Hildreth et al. |
| 7,772,448 B2 | * | 8/2010 | Clark ....................... C07C 2/66 |
| | | | 585/449 |
| 8,258,360 B2 | | 9/2012 | Clark et al. |
| 8,309,778 B2 | | 11/2012 | Wang et al. |
| 2005/0194289 A1 | | 9/2005 | Overbeek et al. |
| 2008/0255398 A1 | | 10/2008 | Stevenson et al. |
| 2008/0293990 A1 | | 11/2008 | Stevenson et al. |

(Continued)

FOREIGN PATENT DOCUMENTS

| EP | 0192059 A1 | 8/1986 | |
| GB | 2162082 A | 1/1986 | |
| WO | WO-9400409 A1 * | 1/1994 | ............. C10G 29/16 |
| WO | 0244306 A1 | 6/2002 | |
| WO | 2004013095 A2 | 2/2004 | |
| WO | 2005085157 A1 | 9/2005 | |
| WO | 2007055488 A1 | 5/2007 | |
| WO | 2013182534 A1 | 12/2013 | |

OTHER PUBLICATIONS

HollyFrontier Safety Data Sheet Naphtha. Jul. 25, 2014. pp. 1-14 (Year: 2014).*
Alfke et al., "Oil Refining", Ullmann's Encyclopedia of Industrial Chemistry, 2007, 55 pages.

(Continued)

*Primary Examiner* — In Suk C Bullock
*Assistant Examiner* — Alyssa L Cepluch
(74) *Attorney, Agent, or Firm* — Cantor Colburn LLP

(57) ABSTRACT

The present invention relates to a process for producing benzene from a mixed hydrocarbon feedstream comprising subjecting C6 cut separated from said mixed hydrocarbon feedstream to aromatization to provide a benzene-rich aromatic stream and recovering the benzene from the benzene-rich aromatic stream.

20 Claims, No Drawings

(56) References Cited

U.S. PATENT DOCUMENTS

| | | | |
|---|---|---|---|
| 2011/0132804 A1* | 6/2011 | Stevenson | B01J 29/047 208/65 |
| 2012/0149958 A1 | 6/2012 | Ellrich et al. | |
| 2013/0338410 A1 | 12/2013 | Wang et al. | |
| 2017/0144946 A1 | 5/2017 | Daniëls et al. | |

OTHER PUBLICATIONS

Encyclopaedia of Hydrocarbons, "Aromatics: Aromatics production and use", 2006, vol. II, Refining and Petrochemicals, Chapter 10.6, pp. 591-614.

Hwang, et al., "Cumene—Kirk Othmer Encyclopedia of Chemical Technology", 2010, pp. 1-10.

International Search Report for International Application No. PCT/EP2015/064314; dated Sep. 9, 2015; 5 Pages.

Laredo et al., "Benzene reduction in gasoline by alkylation with olefins: Effect of the feedstock on the catalyst deactivation", Catalysis A: General, 2009, vol. 363, pp. 11-18.

Nagamori et al., "Converting light hydrocarbons containing olefins to aromatics (Alpha Process)", Microporous and Mesoporous Materials, 1998, vol. 21, pp. 439-445.

Vora et al., "Alkylation—Kirk Othmer Encyclopedia of Chemical Technology", 2003, vol. 2, 35 pages.

Written Opinion of the International Search Report for International Application No. PCT/EP2015/064314; dated Sep. 9, 2015; 6 Pages.

Laredo et al., "Benzene reduction in gasoline by olefin alkylation: Effect of the catalyst on a C6-reformate heart-cut", Catalysis A: General, 2009, vol. 363, pp. 19-26.

\* cited by examiner

PROCESS FOR PRODUCING PURIFIED AROMATIC HYDROCARBONS FROM A MIXED HYDROCARBON FEEDSTREAM

CROSS REFERENCE TO RELATED APPLICATIONS

This application is a 371 of International Application No. PCT/EP2015/064314, filed Jun. 25, 2015, which claims priority to European Application No. 14174373.2 filed Jun. 26, 2014, both of which are incorporated herein by reference in their entirety.

The present invention relates to a process for producing benzene from a mixed hydrocarbon feedstream comprising subjecting C6 cut separated from said mixed hydrocarbon feedstream to aromatization to provide a benzene-rich aromatic stream and recovering the benzene from the benzene-rich aromatic stream.

The commercial production of the benzene derivatives ethylbenzene or cumene comprises the alkylation of benzene using ethylene or propylene as alkylation agent; see e.g. Hwang and Chen (2010) Cumene Kirk-Othmer Encyclopedia of Chemical Technology 1-10. Direct alkylation of a mixed C6 hydrocarbon feedstream is not a viable method to produce high-purity ethylbenzene or cumene since in such a process many undesired by-products are produced which are difficult to separate from the desired aromatic alkylation products; see e.g. U.S. Pat. No. 6,177,600. Therefore, a mixed hydrocarbon feedstream such as reformate or C6 cut conventionally needs to be subjected to aromatic extraction, such as liquid extraction or extractive distillation, to remove the benzene co-boilers in order to provide a sufficiently purified benzene stream. A drawback of such a process for producing benzene is that aromatic extraction methods are expensive and time consuming. Moreover, such conventional methods are not capable of increasing the benzene content in the mixed hydrocarbon feedstream.

It was an object of the present invention to provide an improved process for producing high-purity benzene from a mixed hydrocarbon.

The solution to the above problem is achieved by providing the embodiments as described herein below and as characterized in the claims. Accordingly, the present invention provides a process for producing benzene comprising:
(a) subjecting a mixed hydrocarbon feedstream to a separation to provide a C6 cut;
(b) subjecting C6 cut to aromatization to provide a benzene-rich aromatic stream; and
(c) recovering the benzene from the benzene-rich aromatic stream.

In the context of the present invention, it was surprisingly found that by subjecting the C6 cut separated from a mixed hydrocarbon stream, such as reformate, to aromatization, the paraffins can be selectively cyclized towards benzene, thereby significantly increasing the benzene content of the feedstream. Subsequently the benzene rich C6 cut is subjected to benzene recovery to produce an on-spec benzene stream.

The term "aromatic hydrocarbons" or "aromatics" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

As used herein, the term "C # hydrocarbons", or "C #", wherein "#" is a positive integer, is meant to describe all hydrocarbons having # carbon atoms. Moreover, the term "C #+ hydrocarbons" is meant to describe all hydrocarbon molecules having # or more carbon atoms. Accordingly, the term "C9+ hydrocarbons" is meant to describe a mixture of hydrocarbons having 9 or more carbon atoms. The term "C9+ alkanes" accordingly relates to alkanes having 9 or more carbon atoms.

In the process of the present invention, any mixed hydrocarbon composition that comprises C6 hydrocarbons and that is suitable to be subjected to aromatization can be used as a feedstream. Such a suitable feedstream may be selected from the group consisting of reformate, C6 cut, straight run naphtha, hydrocracked gasoline, light coker naphtha, coke oven light oil and FCC gasoline, or mixtures thereof.

Preferably, the feedstream comprises reformate.

The process of the present invention comprises subjecting a mixed hydrocarbon feedstream to a separation to provide a C6 cut. As used herein, the term "C6 cut" relates to a hydrocarbon fraction comprising at least 60 wt-% C6 hydrocarbons, preferably at least at least 70 wt-% C6 hydrocarbons, more preferably at least 80 wt-% C6 hydrocarbons, particularly preferably at least 90 wt-% C6 hydrocarbons, more particularly preferably at least 95 wt-% C6 hydrocarbons, and most preferably at least 99 wt-% C6 hydrocarbons. Preferably, the separation to provide a C6 cut does not involve aromatic extraction, such as liquid extraction or extractive distillation. Preferably, the separation to provide a C6 cut involves distillation. The skilled person is capable of selecting the suitable distillation conditions to provide a C6 cut as defined herein. Preferably, the distillation conditions are suitable to provide a C6 cut having a boiling point range of 45-90° C., more preferably of 47-87° C., particularly preferably of 48-85° C. and most preferably 49-81° C. A C6 cut from reformate can vary a lot in composition. Preferably, the benzene content of the C6 cut varies between 10-50 wt % with the remainder being mainly paraffins, of which iso-paraffins are much more dominant. The naphthene content is rather low (preferably less than 10 wt %), particularly when the feedstream comprises reformate since refinery reformers dehydrogenate the naphthenic species almost completely. The hydrocarbons comprised in the mixed hydrocarbon feedstream and which are not comprised in the C6 cut, such as the C7+ cut, may be subjected to further chemical processing or separation or may be used as such. Preferably, the C7+ cut is added to the gasoline blending pool.

The process of the present invention comprises aromatization of the C6 cut to provide a benzene-rich aromatic stream.

Preferably, the aromatization comprises contacting the C6 cut with an aromatization catalyst under aromatization conditions. The process conditions useful for aromatization, also described herein as "aromatization conditions", can be easily determined by the person skilled in the art; see Encyclopaedia of Hydrocarbons (2006) Vol II, Chapter 10.6, p. 591-614.

The term "aromatization" is used herein in its generally accepted sense and thus may be defined as a process to convert aliphatic hydrocarbons to aromatic hydrocarbons. There are many aromatization technologies described in the prior art using C3-C8 aliphatic hydrocarbons as raw material; see e.g. U.S. Pat. Nos. 4,056,575; 4,157,356; 4,180,689; 4,456,527; Micropor. Mesopor. Mater 21, 439; WO 2004/

013095 A2 and WO 2005/085157 A1. Accordingly, the aromatization catalyst may comprise a zeolite, preferably selected from the group consisting of ZSM-5 and zeolite L, and may further comprise one or more elements selected from the group consisting of Ga, Zn, and Ge and a hydrogenation metal which is preferably selected from the group consisting of Pt, Pd, In, Rh, and Ru.

Preferably, the silicon to aluminum atomic ratio (Si:Al) of the zeolite is greater than 2, more preferably in the range from 10 to 200 and even more preferably in the range from 20 to 100. Preferably, the zeolite a medium pore zeolite. Preferably, the average pore size of the zeolite is in the range from 5 to 7 angstroms. Preferably, the zeolite is selected from the group consisting of ZSM-5 and zeolite L. Most preferably, the zeolite is ZSM-5. Preferably, the zeolite comprises Ge as a framework element. Preferably, the germanium content of the zeolite having Ge as framework element is in the range from 0.05% to 10% by weight, more preferably from 2% to 8% by weight and even more preferably in the range of from 0.05% to 3%.

Preferably, the hydrogenation metal is present in the range of from 0.2 wt-% to 2 wt-%, and more preferably in the range of from 0.2 wt-% to 1.5 wt-%. Preferably, the noble metal is platinum, palladium, indium, rhodium or ruthenium and more preferably platinum.

Preferably, the aromatization catalyst used in the process of the present invention is non-acidic. As used herein, the term "non-acidic zeolite" relates to a zeolite that comprises less than 0.2 wt-% Al, preferably less than 0.1 wt-% Al and most preferably less than 0.05 wt-% Al or which has been subjected to base-exchange. Accordingly, the zeolite either comprises substantially no aluminium sites in the zeolite framework or the aluminium sites in the zeolite framework are exchanged with base cations. The zeolite is preferably base-exchanged with an alkali metal or alkaline earth metals such as cesium, potassium, sodium, rubidium, barium, calcium, magnesium and mixtures thereof, most preferably cesium. Base-exchange may take place during synthesis of the zeolite with an alkali metal or alkaline earth metal being added as a component of the reaction mixture or may take place with a crystalline zeolite before or after deposition of a noble metal. The zeolite is base-exchanged to the extent that most or all of the cations associated with aluminum are alkali metal or alkaline earth metal. An example of a monovalent base:aluminum molar ratio in the zeolite after base exchange is at least about 0.9.

The aromatization catalyst preferably is a non-acidic zeolite comprising Ge as a framework element.

The aromatization catalyst preferably is non-acidic by base-exchange and/or further comprises a hydrogenation metal, preferably Pt.

Preferably, the zeolite comprised in the aromatization catalyst is ZSM-5. More preferably, the aromatization catalyst is selected from the group consisting of ZSM-5, Ga/ZSM-5, Zn/ZSM-5 and Pt/GeZSM-5. More preferably, the catalyst is Pt/GeZSM-5. As used herein, the term "Pt/GeZSM-5" is meant to describe a platinum-modified ZSM-5 zeolite comprising Ge as a framework element. The Pt/GeZSM-5 preferably comprises from 0.2 wt-% to 2 wt-% Pt, more preferably from 0.2 wt-% to 1.5 wt-% Pt. Even more preferably, the aromatization catalyst comprises a non-acidic Pt/GeZSM-5 zeolite. Most preferably, the catalyst is Pt/GeZSM-5 that is based-exchanged with Cs as described in WO 2008/127538 A1.

In the context of the present invention, it was surprisingly found that the benzene yield of a process for the aromatization of a C6 cut can be increased by specifically selecting Pt/GeZSM-5 that is based-exchanged with Cs as the aromatization catalyst.

The aromatization conditions preferably comprise a temperature of 400-600° C., preferably 450-550° C. a pressure of 50-1000 kPa gauge, preferably 75-500 kPa gauge, and a Weight Hourly Space Velocity (WHSV) of 0.1-20 h$^{-1}$, preferably of 0.4-4 h$^{-1}$.

Preferably, the aromatization comprises contacting the C6 cut with an aromatization catalyst under aromatization conditions, wherein the aromatization catalyst comprises a zeolite selected from the group consisting of ZSM-5 and zeolite L, optionally further comprising one or more elements selected from the group consisting of Ga, Zn, Ge and Pt and wherein the aromatization conditions comprise a temperature of 400-600° C., preferably 450-550° C. a pressure of 50-1000 kPa gauge, preferably 75-500 kPa gauge, and a Weight Hourly Space Velocity (WHSV) of 0.1-20 h$^{-1}$, preferably of 0.4-4 h$^{-1}$.

It may be required to subject the mixed hydrocarbon feedstream and/or the C6 cut to desulphurization to prevent deactivation of the aromatization catalyst. This is particularly important in case a feedstream is selected that is relatively rich in sulfur compounds such as straight run naphtha, light coker naphtha, coke oven light oil or mixtures thereof. Moreover, particular aromatization catalyst are particularly sensitive for deactivation by sulfur compounds such as zeolite L-based catalysts. Means and methods suitable for desulfurization of hydrocarbon streams are well known in the art and include hydrodesulfurization. Such a hydrodesulfurization process is performed in a "HDS unit" or "hydrotreater"; see Alfke et al. (2007) Oil Refining, Ullmann's Encyclopedia of Industrial Chemistry. Generally, the hydrodesulfurization reaction takes place in a fixed-bed reactor at elevated temperatures of 200-425° C., preferably of 300-400° C. and elevated pressures of 1-20 MPa gauge, preferably 1-13 MPa gauge in the presence of a catalyst comprising elements selected from the group consisting of Ni, Mo, Co, W and Pt, with or without promoters, supported on alumina, wherein the catalyst is in a sulfide form. Preferably, the C6 cut that is contacted with the aromatization catalyst comprises less than 5 wt-ppm sulfur, more preferably less than 1 wt-ppm sulfur. In case zeolite L-based aromatization catalysts is selected, the sulfur content of the C6 cut that is contacted with the aromatization catalyst preferably comprises less than 50 wt-ppb sulfur, more preferably less than 10 wt-ppb sulfur. In case a non-acidic zeolite comprising Ge as a framework element is selected as aromatization catalyst, sulfur content of the C6 cut that is contacted with the aromatization catalyst preferably comprises less than 50 wt-ppm of sulfur, more preferably less than 10 wt-ppm of sulfur and most preferably less than 2 wt-ppm of sulfur. Accordingly, an advantage of selecting a non-acidic zeolite comprising Ge as a framework element as aromatization catalyst is that this catalyst is more resistant to sulfur impurities in the feed.

The process of the present invention involves recovering the benzene from the benzene-rich stream that is obtained by subjecting the C6 cut to aromatization. As used herein, the term "benzene-rich aromatic stream" relates to the product stream obtained when subjecting a C6 cut to aromatization. Preferably, the benzene-rich aromatic stream comprises at least 50 wt-% benzene, preferably at least 60 wt-% benzene, more preferably at least at least 70 wt-% benzene, even more preferably at least 80 wt-% benzene, particularly preferably at least 90 wt-% benzene, more particularly preferably at least 95 wt-% C6 benzene, and most preferably at least 99 wt-% benzene. Any known means for separating benzene from a mixed hydrocarbon stream may be employed in the process of the present invention. Preferably, the benzene recovery does not involve aromatic extraction, such as liquid extraction or extractive distillation. Preferably, the benzene recovery involves distillation. The C6 non aromatic hydrocarbon compounds comprised benzene-rich aromatic stream may be recycled to the aromatization reactor after benzene recovery.

Preferably, the benzene-rich aromatic stream in step (c) is subjected to hydrocracking to produce a product stream comprising benzene and C1-C4 hydrocarbons.

In the context of the present invention, it was surprisingly found that the benzene yield of the overall process could be improved by subjecting the benzene-rich aromatic stream obtained by aromatization of the C6 cut to hydrocracking to produce a product stream comprising benzene and C1-C4 hydrocarbons. A further advantage of subjecting the benzene-rich aromatic stream to hydrocracking is that eventual traces of benzene co-boilers that may be comprised in the benzene-rich aromatic stream are removed.

Accordingly, the process of the present invention may involve hydrocracking, which comprises contacting the benzene-rich aromatic stream in the presence of hydrogen with a hydrocracking catalyst under hydrocracking conditions. The process conditions useful hydrocracking, also described herein as "hydrocracking conditions", can be easily determined by the person skilled in the art; see e.g. Alfke et al. (2007) loc. cit.

The term "hydrocracking" is used herein in its generally accepted sense and thus may be defined as a catalytic cracking process assisted by the presence of an elevated partial pressure of hydrogen; see e.g. Alfke et al. (2007) loc.cit. The products of the hydrocracking process step are LPG and benzene. The process conditions used for hydrocracking generally includes a process temperature of 200-600° C., elevated pressures of 0.2-20 MPa, space velocities between 0.1-20 $h^{-1}$. Hydrocracking reactions proceed through a bifunctional mechanism which requires an acid function, which provides for the cracking and isomerization and which provides breaking and/or rearrangement of the carbon-carbon bonds comprised in the hydrocarbon compounds comprised in the feed, and a hydrogenation function. Many catalysts used for the hydrocracking process are formed by combining various transition metals, or metal sulfides with the solid support such as alumina, silica, alumina-silica, magnesia and zeolites.

Preferably the benzene is recovered from benzene-rich aromatic stream by subjecting said benzene-rich aromatic stream to gasoline hydrocracking. As used herein, the term "gasoline hydrocracking" or "GHC" refers to a hydrocracking process that is particularly suitable for converting a complex hydrocarbon feed that is relatively rich in aromatic hydrocarbon compounds—such as benzene-rich aromatic stream obtained in the process of the present invention—to LPG and benzene, wherein said process is optimized to keep one aromatic ring intact of the aromatics comprised in the GHC feedstream, but to remove most of the side-chains from said aromatic ring. Accordingly, the main product produced by gasoline hydrocracking is benzene and the process can be optimized to provide chemicals-grade benzene. Preferably, the gasoline hydrocracking conditions include a temperature of 300-580° C., more preferably of 400-580° C. and even more preferably of 430-530° C. Lower temperatures must be avoided since hydrogenation of the aromatic ring becomes favourable, unless a specifically adapted hydrocracking catalyst is employed. For instance, in case the catalyst comprises a further element that reduces the hydrogenation activity of the catalyst, such as tin, lead or bismuth, lower temperatures may be selected for gasoline hydrocracking; see e.g. WO 02/44306 A1 and WO 2007/055488. In case the reaction temperature is too high, the yield of LPG's (especially propane and butanes) declines and the yield of methane rises. As the catalyst activity may decline over the lifetime of the catalyst, it is advantageous to increase the reactor temperature gradually over the life time of the catalyst to maintain the hydrocracking conversion rate. This means that the optimum temperature at the start of an operating cycle preferably is at the lower end of the hydrocracking temperature range. The optimum reactor temperature will rise as the catalyst deactivates so that at the end of a cycle (shortly before the catalyst is replaced or regenerated) the temperature preferably is selected at the higher end of the hydrocracking temperature range.

Preferably, the gasoline hydrocracking of the benzene-rich aromatic stream is performed at a pressure of 0.3-5 MPa gauge, more preferably at a pressure of 0.6-3 MPa gauge, particularly preferably at a pressure of 1-2 MPa gauge and most preferably at a pressure of 1.2-1.6 MPa gauge. By increasing reactor pressure, conversion of C5+ non-aromatics can be increased, but this also increases the yield of methane and the hydrogenation of aromatic rings to cyclohexane species which can be cracked to LPG species. This results in a reduction in benzene yield as the pressure is increased and, as some cyclohexane and its isomer methylcyclopentane are not fully hydrocracked, there is an optimum in the purity of the resultant benzene at a pressure of 1.2-1.6 MPa.

Preferably, gasoline hydrocracking of a hydrocarbon feedstream is performed at a Weight Hourly Space Velocity (WHSV) of 0.1-20 $h^{-1}$, more preferably at a Weight Hourly Space Velocity of 0.2-15 $h^{-1}$ and most preferably at a Weight Hourly Space Velocity of 0.4-10 $h^{-1}$. When the space velocity is too high, not all benzene co-boiling paraffin components are hydrocracked, so it will not be possible to achieve benzene specification by simple distillation of the reactor product. At too low space velocity the yield of methane rises at the expense of propane and butane. By selecting the optimal Weight Hourly Space Velocity, it was surprisingly found that sufficiently complete reaction of the benzene co-boilers is achieved to produce on spec benzene without the need for a liquid recycle.

Preferably, the hydrocracking comprises contacting the benzene-rich aromatic stream in the presence of hydrogen with a hydrocracking catalyst under hydrocracking conditions, wherein the hydrocracking catalyst comprises 0.01-1 wt-% hydrogenation metal in relation to the total catalyst weight and a zeolite having a pore size of 5-8 Å and a silica ($SiO_2$) to alumina ($Al_2O_3$) molar ratio of 5-200 and wherein the hydrocracking conditions comprise a temperature of 400-580° C., a pressure of 300-5000 kPa gauge and a Weight Hourly Space Velocity (WHSV) of 0.1-20 $h^{-1}$. The hydrogenation metal preferably is at least one element selected from Group 10 of the periodic table of Elements, most preferably Pt. The zeolite preferably is MFI. Preferably a temperature of 420-550° C., a pressure of 600-3000 kPa gauge and a Weight Hourly Space Velocity of 0.2-15 $h^{-1}$ and more preferably a temperature of 430-530° C., a pressure of 1000-2000 kPa gauge and a Weight Hourly Space Velocity of 0.4-10 $h^{-1}$ is used.

Accordingly, preferred gasoline hydrocracking conditions thus include a temperature of 400-580° C., a pressure of 0.3-5 MPa gauge and a Weight Hourly Space Velocity of 0.1-20 $h^{-1}$. More preferred gasoline hydrocracking conditions include a temperature of 420-550° C., a pressure of 0.6-3 MPa gauge and a Weight Hourly Space Velocity of 0.2-15 $h^{-1}$. Particularly preferred gasoline hydrocracking conditions include a temperature of 430-530° C., a pressure of 1-2 MPa gauge and a Weight Hourly Space Velocity of 0.4-10 $h^{-1}$.

Accordingly, the hydrocracking preferably comprises contacting the benzene-rich aromatic stream in the presence of hydrogen with a hydrocracking catalyst under hydrocracking conditions.

The hydrocracking catalyst preferably comprises 0.01-1 wt-% hydrogenation metal in relation to the total catalyst weight and a zeolite having a pore size of 5-8 Å and a silica ($SiO_2$) to alumina ($Al_2O_3$) molar ratio of 5-200.

The hydrocracking conditions preferably comprise a temperature of 450-580° C., a pressure of 300-5000 kPa gauge and a Weight Hourly Space Velocity (WHSV) of 0.1-20 $h^{-1}$.

Optionally, the benzene-rich aromatic stream obtained by aromatization of the C6 cut is directly subjected to the hydrocracking without subjecting said benzene-rich aromatic stream to any kind of separation. Preferably, the aromatization produces sufficient hydrogen for the hydrocracking.

When the benzene-rich aromatic stream obtained by aromatization of the C6 cut is subjected to hydrocracking to produce a product stream comprising benzene and C1-C4 hydrocarbons, the benzene is preferably separated from the C1-C4 hydrocarbons by vapor-liquid separation.

The benzene stream obtained by the benzene recovery comprised in the process of the present invention preferably comprises at least 95 wt-% benzene, more preferably at least 98 wt-% benzene, particularly preferably at least 99 wt-% benzene and most preferably at least 99.8 wt-% benzene.

The process of the present invention preferably further comprises subjecting the benzene to alkylation to produce an alkylated aromatic stream.

Accordingly, the process of the present invention may involve alkylation, which comprises contacting the benzene with an alkylation agent in the presence of an alkylation catalyst under alkylation conditions. The process conditions useful alkylation, also described herein as "alkylation conditions", can be easily determined by the person skilled in the art; see e.g. Vora et al. (2003) Alkylation Kirk-Othmer Encyclopedia of Chemical Technology and Hwang and Chen (2010) loc. cit. The process conditions used for alkylation generally includes a process temperature of 100-300° C., a pressure of 0.5-10 MPa, a weight hourly space velocity of 0.5-20 $h^{-1}$ and benzene/alkylation agent molar ratio of 3-10. The benzene alkylation process step uses an acidic catalyst which may be a solid phosphoric acid catalyst (phosphoric acid supported on alumina) or an aluminum chloride complex as the catalyst or an acidic zeolite-based catalyst. Preferably, the zeolite comprised in the alkylation catalyst has a pore size of 6-8 Å. The optimal process conditions depend on the alkylation agent. For instance, when selecting propylene as the alkylation agent the process conditions are somewhat milder when compared to selecting ethylene as the alkylation agent.

The alkylation preferably comprises contacting the benzene in the presence of ethylene with an alkylation catalyst under alkylation conditions to produce ethylbenzene, wherein said alkylation catalyst comprises beta zeolite, zeolite Y, ZSM-12, MCM-22 and mordenite and wherein said alkylation conditions comprise a temperature of 120-250° C. preferably of 150-230° C. a pressure of 1000-5000 kPa, preferably of 2500-3500 kPa, a Weight Hourly Space Velocity (WHSV) of 0.5-20 $h^{-1}$, preferably of 1-10 $h^{-1}$ and a benzene/ethylene molar ratio of 2-10, preferably of 2-8.

Alternatively, the alkylation preferably comprises contacting the benzene in the presence of propylene with an alkylation catalyst under alkylation conditions to produce cumene, wherein said alkylation catalyst comprises a zeolite selected from the group consisting of beta zeolite, zeolite Y, ZSM-12, MCM-22 and mordenite and wherein said alkylation conditions comprise a temperature of 120-250° C. preferably of 150-230° C. a pressure of 1000-5000 kPa, preferably of 2500-3500 kPa, a Weight Hourly Space Velocity (WHSV) of 0.5-20 $h^{-1}$, preferably of 1-10 $h^{-1}$ and a benzene/propylene molar ratio of 3-10, preferably of 5-8.

Optionally, the benzene-rich aromatic stream obtained by aromatization of the C6 cut is directly subjected to alkylation using ethylene or propylene as alkylation agent, without subjecting said benzene-rich aromatic stream to any kind of separation.

Preferably, the alkylated aromatic stream is subjected to a separation to provide a monoalkylated aromatic product stream and stream comprising polyalkylated aromatic product stream and wherein said is recycled to the hydrocracking.

It is noted that the invention relates to all possible combinations of features described herein, particularly features recited in the claims.

It is further noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention will now be more fully described by the following non-limiting Examples.

EXAMPLE 1

Cs-exchanged Pt/GeZSM-5 Aromatization Catalyst

This catalyst consists of Pt dispersed on a basic ZSM-5 zeolite containing framework germanium (1% Pt/CsGeZSM-5). This catalyst may be prepared as described in U.S. Pat. No. 7,902,413 or US 2008/0293990 A1.

Accordingly, Ge-ZSM-5 Zeolite may be prepared as follows: Solution #1 is made by diluting 15.84 g of 50 wt % NaOH solution with 131.25 g of deionized (DI) water and subsequently dissolving 7.11 g of germanium dioxide. Solution #2 is made by diluting 3.84 g sodium aluminate solution (23.6 wt % alumina and 19.4 wt sodium oxide) with 153.9 g DI water. Solution #1 is added to 150 g Ludox AS-40 (40 wt % silica in a colloidal state) and vigorously stirred for 10 minutes to obtain a homogeneous mixture. Solution #2 is stirred into this mixture. After 15 minutes of vigorous agitation, 105.42 g of tetra-n-propyl ammonium hydroxide (TPAOH) is added and the mixture is stirred for 60 minutes. Finally, 23.32 g of glacial acetic acid is added to the gel to adjust the pH of the mixture to about 9. This mixture is loaded into a 1 L stainless steel autoclave and heated at 160° C. for 36 hours with stirring. Subsequently, the solids obtained are filtered from the mother liquor and washed with DI water. The solid is calcined at 550° C. for 6 hours in an oven with air flow. The MFI structure of the solid can be confirmed by measuring the powder X-Ray diffraction pattern.

8 grams of GeZSM-5 prepared as described above are washed with 200 ml of aqueous $CsNO_3$ (0.5M) then filtered.

The filtrate is then rewashed 3 more times with 0.5M $CsNO_3$ and rinsed with distilled $H_2O$ on the final filtering. The zeolite powder is then calcined for 3 hours at 280° C. in air. Incipient wetness impregnation is carried out by adding drop wise a solution of 0.069 g $Pt(NH_2)_4(NO_3)_2$ dissolved in 1.343 g of deionized water to 3.508 grams of the Cs-exchanged Ge ZSM-5. The material is dried for 1 hour in a 110° C. drying oven then calcined at 280° C. for 3 hours. A representative elemental analysis gives 39.92 wt % Si, 0.69 wt % Al, 4.14 wt Ge, 5.03 wt % Cs, and 0.90 wt % Pt. The catalyst powder is typically pressed and sized to 20-40 mesh.

EXAMPLE 2

Aromatization of C6 Heart Cut

The experimental data as provided herein were obtained by modelling the product slates of an aromatization unit fed with reformate C6 heart cut feed. In this aromatization isohexanes ("iso-C6") and normal hexanes ("n-C6") are transformed into benzene, naphthenic species are dehydrogenated into benzene.

Reaction tests are carried out using a 0.31 inch ID reactor tube containing a catalyst bed comprising 1 to 4.32 $cm^3$ of the aromatization catalysts as described above in Examples 1 and 2. The bed is diluted to a total of 8 $cm^3$ with inert silicon carbide to maintain constant length. Liquid n hexane is vaporized and passed over the catalyst bed at temperatures ranging from 500 to 540° C., pressures between 103 kPa absolute (15 psia) and 310 kPa absolute (45 psia), and liquid hourly space velocities ranging from 1 to 8 $hr^{-1}$. Products are analysed by on-line gas chromatography. Further experiments are carried out in two adiabatic pilot reactors connected in series, where n-hexane or light naphtha is vaporized and passed over a bed containing 80 g of catalyst per reactor, at an inlet temperature of 540° C., outlet temperatures at or above 450° C., and pressures ranging from 241 kPa absolute (35 psia) to 62 kPa absolute (9 psia). For these experiments, products are analysed both by on-line gas chromatography and by off-line analysis of collected liquid samples.

The experimental data as provided herein were obtained by modelling the product slates of an aromatization unit fed with reformate C6 heart cut feed. In this example three cases are considered, i.e. a low, medium and high benzene concentration in the c6 heart cut feed. One-pass experiments allow the estimation of what conversions would be obtained in a complete process using partial recycle of unconverted hexanes; the predicted conversions are shown in Table 1:

TABLE 1

Conversions for C6 hydrocarbons obtained in aromatization experiment described above.

|  | % |
|---|---|
| Benzene | 0 |
| iso-C6 | 25 |
| n-C6 | 75 |
| cyclo-C6 | 100 |

A C6 cut from reformate may vary in composition. Roughly, the benzene content varies between 10-50 wt % with the remainder being mainly paraffins, of which isoparaffins are much more dominant. The naphthene content (mainly cyclohexane "cyclo-C6") typically is below 10 wt % since refinery reformers dehydrogenate the naphthenic species almost completely.

TABLE 2

Three feed scenarios modelled in this example
C6 heart cut feed composition (wt %)

|  | LOW | MEDIUM | HIGH |
|---|---|---|---|
| Benzene | 17 | 35 | 50 |
| iso-C6 | 56 | 44 | 34 |
| n-C6 | 22 | 17 | 13 |
| cyclo-C6 | 5 | 4 | 3 |
| Sum | 100 | 100 | 100 |

Based on the examples explained above and given the obtained conversions explained in table 1 the following product slates are modelled for the three feed scenario's described in table 2.

The tables below indicate the estimated effluent composition of an aromatization unit with Cs-exchanged Pt/GeZSM-5 aromatization catalyst.

TABLE 3

LNA effluent composition in aromatization unit with using Cs-exchanged Pt/GeZSM-5 aromatization catalyst as described in Example 1. All numbers in wt %.
LNA effluent composition

|  | LOW | MEDIUM | HIGH |
|---|---|---|---|
| Benzene | 46 | 58 | 70 |
| iso-C6 | 42 | 33 | 25 |
| n-C6 | 6 | 4 | 3 |
| cyclo-C6 | 0 | 0 | 0 |
| Hydrogen & Light gases (C1-C4) | 6.5 | 4.8 | 1.4 |

Accordingly, it was found that n-C6, cyclo-C6 and the iso-C6 comprised in the C6 heart cut are converted into benzene when using a Cs-exchanged Pt/GeZSM-5 aromatization catalyst.

EXAMPLE 3

Aromatic Alkylation

The benzene rich effluent stream from the aromatization unit is subsequently subjected to an alkylation unit where an olefins source is added to alkylate the benzene to ethylbenzene and/or cumene. The alkylation process step is modelled based on literature data published in Laredo et al. (2009) Applied Catalysis A: General 363, 11-18. Accordingly, the benzene rich effluent stream from the aromatization unit is subjected to an alkylation unit loaded with zeolite Beta (220° C., 3100-4800 kPa and benzene-to-olefin ratio of 2), where EB and cumene are produced with approximately 50% conversion (Laredo et al. (2009) loc. cit).

The major advantage of boosting the benzene concentration by means of an aromatization unit is the fact that less tonne of C6 heart cut feedstock is required to produce one tonne of cumene/ethylbenzene. Secondly when using an aromatization unit containing the Cs-exchanged Pt/GeZSM-5 aromatization catalysts then the benzene concentration is even higher resulting in a further decrease of required C6 heart cut feedstock per tonne of cumene/ethylbenzene. This is illustrated by the numbers in the table below.

| Case | | LOW | MEDIUM | HIGH |
|---|---|---|---|---|
| 1 | Required feedstock/tonne of cumene without aromatization unit (tonne C6 feed/tonne cumene) | 3.8 | 1.9 | 1.3 |
| 2 | Required feedstock/tonne of cumene with aromatization unit with Cs-exchanged Pt/GeZSM-5 catalyst (tonne C6 feed/tonne cumene) | 1.4 | 1.1 | 0.9 |

The LOW, MEDIUM and HIGH cases refer to the benzene concentration in the C6 heart cut feed.

Comparing case 1 and 2 illustrates the fact that processing the C6 heart cut feed in an aromatization unit results in a lower overall feed consumption per tonne of cumene.

In the context of the present invention, it was further surprisingly found that the aromatization catalysts considered have an improved carbon number preservation. This can be exploited to increase the benzene concentration in a C6 heart cut from reformate since this C6 cut contains a significant amount of paraffins (iso+normal). By feeding this C6 cut to an aromatization unit using a Cs-exchanged Pt/GeZSM-5 aromatization catalyst, the benzene concentration can be increased significantly. The main benefit of the Cs-exchanged Pt/GeZSM-5 aromatization catalyst compared to other known aromatization catalysts is the fact that the Cs-exchanged Pt/GeZSM-5 catalysts also aromatizes iso-paraffins, iso-hexanes to benzene in our case.

The invention claimed is:

1. A process for producing benzene comprising:
   (a) subjecting a mixed hydrocarbon feedstream to a separation to provide a C6 cut, wherein the mixed hydrocarbon feedstream comprises reformats, and wherein a benzene content of the C6 cut comprises 10-50 wt % benzene;
   (b) subjecting the C6 cut to aromatization to provide a benzene-rich aromatic stream; and
   (c) separating and recovering a benzene stream from the benzene-rich aromatic stream without using aromatic extraction.

2. The process according claim 1, wherein in step (c) further comprises subjecting the benzene-rich aromatic stream to hydrocracking to produce a product stream comprising benzene and C1-C4 hydrocarbons.

3. The process according to claim 2, wherein the separating comprises separating the benzene stream from the C1-C4 hydrocarbons by vapor-liquid separation.

4. The process according to claim 1, wherein the aromatization comprises contacting the C6 cut with an aromatization catalyst under aromatization conditions.

5. The process according to claim 4, wherein the aromatization conditions comprise a temperature of 400-600° C., a pressure of 50-1000 kPa gauge, and a Weight Hourly Space Velocity (WHSV) of 0.1-20 $h^{-1}$.

6. The process according to claim 2, wherein the hydrocracking comprises contacting the benzene-rich aromatic stream in the presence of hydrogen with a hydrocracking catalyst under hydrocracking conditions.

7. The process according to claim 6, wherein the hydrocracking conditions comprise a temperature of 450-580° C., a pressure of 300-5000 kPa gauge and a Weight Hourly Space Velocity (WHSV) of 0.1-20 $h^{-1}$.

8. The process according to claim 1, wherein the feedstream further comprises hydrocracked gasoline.

9. The process according to claim 2, wherein the process further comprises subjecting the benzene stream to alkylation to produce an alkylated aromatic stream.

10. The process according to claim 9, wherein the alkylation comprises contacting the benzene stream in the presence of ethylene with an alkylation catalyst under alkylation conditions to produce ethylbenzene, wherein said alkylation catalyst comprises beta zeolite, zeolite Y, ZSM-12, MCM-22 or mordenite and wherein said alkylation conditions comprise a temperature of 120-250° C., a pressure of 1000-5000 kPa, a Weight Hourly Space Velocity (WHSV) of 0.5-20 $h^{-1}$, and a benzene/ethylene molar ratio of 2-10.

11. The process according to claim 9, wherein the alkylation comprises contacting the benzene stream in the presence of propylene with an alkylation catalyst under alkylation conditions to produce cumene, wherein said alkylation catalyst comprises a zeolite selected from the group consisting of beta zeolite, zeolite Y, ZSM-12, MCM-22 and mordenite and wherein said alkylation conditions comprise a temperature of 120-250° C., a pressure of 1000-5000 kPa, a Weight Hourly Space Velocity (WHSV) of 0.5-20 $h^{-1}$, and a benzene/propylene molar ratio of 3-10.

12. The process according to claim 9, wherein the alkylated aromatic stream is subjected to a separation to provide a monoalkylated aromatic product stream and a stream comprising polyalkylated aromatic product and wherein said polyalkylated aromatic product is recycled to the hydrocracking.

13. The process according to claim 5, wherein the aromatization conditions comprise a temperature of 450-550° C. and a pressure of 75-500 kPa gauge.

14. The process according to claim 10, wherein said alkylation conditions comprise a temperature of 150-230° C., a pressure of 2500-3500 kPa, a Weight Hourly Space Velocity (WHSV) of 1-10 $h^{-1}$, and a benzene/ethylene molar ratio of 2-8.

15. The process according to claim 11, wherein said alkylation conditions comprise a temperature of 150-230° C., a pressure of 2500-3500 kPa, a Weight Hourly Space Velocity (WHSV) of 1-10 $h^{-1}$, and a benzene/propylene molar ratio of 5-8.

16. The process according to claim 1, wherein the C6 cut comprises at least 95 wt-% C6 hydrocarbons.

17. The process according to claim 1, wherein the benzene content of the C6 cut comprises 17-50 wt %.

18. The process according to claim 1, wherein the benzene content of the C6 cut comprises 35-50 wt % benzene.

19. The process according to claim 1, wherein separating and recovering the benzene stream from the benzene-rich aromatic stream is done without extractive distillation.

20. The process according to claim 1, wherein separating and recovering the benzene stream from the benzene-rich aromatic stream is done without liquid extraction.

* * * * *

UNITED STATES PATENT AND TRADEMARK OFFICE
CERTIFICATE OF CORRECTION

| | | |
|---|---|---|
| PATENT NO. | : 10,717,688 B2 | |
| APPLICATION NO. | : 15/321501 | |
| DATED | : July 21, 2020 | |
| INVENTOR(S) | : Scott Stevenson and Dimitri Daniels | |

It is certified that error appears in the above-identified patent and that said Letters Patent is hereby corrected as shown below:

In the Claims

In Column 11, Line 33, in Claim 1, please delete "reformats" and replace with -- reformate --.

Signed and Sealed this
Twenty-fourth Day of May, 2022

Katherine Kelly Vidal
*Director of the United States Patent and Trademark Office*